US00PP24988P3

(12) United States Plant Patent
Suphachadiwong

(10) Patent No.: US PP24,988 P3
(45) Date of Patent: Oct. 21, 2014

(54) *VANDA* PLANT NAMED 'SPCDW1110'

(50) Latin Name: ***Vanda* hybrid**
Varietal Denomination: SPCDW1110

(75) Inventor: Thumrong Suphachadiwong, Chonburi (TH)

(73) Assignee: Suphatchatwong Innovation (TH)

( * ) Notice: Subject to any disclaimer, the term of this patent is extended or adjusted under 35 U.S.C. 154(b) by 200 days.

(21) Appl. No.: 13/573,355

(22) Filed: Sep. 10, 2012

(65) Prior Publication Data

US 2013/0067625 P1 Mar. 14, 2013

(30) Foreign Application Priority Data

Sep. 12, 2011 (QZ) ..... PBR 2011/2168

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Vanda* cultivar named 'SPCDW1110' is disclosed, characterized by petals and sepals colored white with violet-Blue netting and a widefloral lip. The new variety is a *Vanda*, typically produced as an indoor ornamental plant.

1 Drawing Sheet

Latin name of the genus and species: *Vanda* hybrid.
Variety denomination: 'SPCDW1110'.

BACKGROUND OF THE INVENTION

This application relates to a new cultivar of *Vanda*, as described in EU application number 2011/2168, filed Sep. 12, 2011, grant pending, to which applicant claims priority. The new variety is the product of a planned breeding program. The new variety originated as a seedling from the crossing of the unpatented, proprietary seed parent *Vanda* 'RR-CS221' with the unpatented, proprietary pollen parent referred to as *Vanda* 'C832221'. The crossing was made by the inventor in his research greenhouse in Chonburi, Thailand in October of 1987.

The new variety was first selected by the inventor, Thumrong Suphachadiwong, a citizen of Thailand, in February 1998, in a research greenhouse belonging to the inventor in Chonburi, Thailand. After identifying the new variety as a potentially interesting selection, the inventor continued confidential testing and propagation of 'SPCDW1110', assessing stability of the unique characteristics of this variety.

Asexual reproduction of the new cultivar 'SPCDW1110' was first performed at a commercial laboratory belonging to the inventor in Chonburi, Thailand by tissue culture in March of 1999. Access to all plants was restricted, as plants were kept in a greenhouse not open to the public, and tissue culture plantlets were in a laboratory belonging to the inventor, and not accessible to the public. Through subsequent propagation by vegetative cuttings, multiple generations have been reproduced, which have shown that the unique features of this cultivar are stable and reproduced true to type.

SUMMARY OF THE INVENTION

The cultivar 'SPCDW1110' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1110.' These characteristics in combination distinguish 'SPCDW1110' as a new and distinct *Vanda* cultivar:

1. Unique sepal and petal coloration of white with violet-blue netting.
2. Improved plant compatibility for commercial growing methods.
3. Wide floral lip.
4. Definite, clean netting lines of the sepals and petals.

PARENT COMPARISON

Plants of the new cultivar 'SPCDW1110' are similar to the seed parent, *Vanda* 'RR-CS221' in most horticultural characteristics. The new variety, however, produces flowers with a different color than the seed parent.

Plants of the new cultivar 'SPCDW1110' are similar to the pollen parent, *Vanda* 'C832221' in most horticultural characteristics. Plants of the new variety, however, are larger, with a longer leaf span than the pollen parent.

COMMERCIAL COMPARISON

'SPCDW1110' is similar in most horticultural characteristics to the unpatented commercial variety *Vanda* 'Blue Magic' in most horticultural characteristics. The new variety, however, produces sepals and petals colored white with violet-blue netting whereas 'Blue Magic' produces petals and sepals that are white with thick, dark purple netting. The new variety has a wider lip than 'Blue Magic'. Additionally, the netting of the new variety is expressed in a more definite, clear pattern than that of 'Blue Magic'.

BRIEF DESCRIPTION OF THE PHOTOGRAPH

The accompanying photograph in FIG. 1 illustrates in full color a typical plant of 'SPCDW1110' grown in a commercial greenhouse in Honselersdijk, the Netherlands. This plant is approximately 5.5 years old, shown planted in a 8 by 8 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SPCDW1110' plants grown in a greenhouse in Honselersdijk, the Netherlands. Temperatures ranged were approximately 23° C. during the day and 19° C. at night. No photoperiodic or chemical treatments were given to the plants. When natural lighting fell below 150 Watt, artificial lighting is given at 10,000 lux for 16 hours a day. Measurements and numerical values represent averages of typical plant types. Botanical classification: *Vanda* hybrid 'SPCDW1110'.

PROPAGATION

Type of propagation typically used: Tissue culture.

Propagation details: The time needed from for the start of a mericlone to get the small plants ready for deflasking is approximately 24 months under a controlled temperature of about 26 degrees Celsius. After that period plants have matured roots. Plants start to make roots in the last 6 months in flasks. After deflasking they remain in a shaded and controlled environment.

Root description: Moderately to heavy rooting with aerial roots only. Roots are very fleshy, non-fibrous.

*Average length of mature roots.*—27.9 cm.

*Average diameter of mature roots.*—2 mm.

*Old roots colored yellow-green.*—Near RHS 146C.

*Young roots colored greyed-green.*—Near RHS 192B.

PLANT

Growth habit: Monopodial, upright.

Height from soil line to top of foliage: Average height from base (plant grown in hanging basket, so no soil line present) to top of foliage: 29.5 cm.

Height from soil line to top of flowers: Average height from base (plant grown in hanging basket, so no soil line present) to top of flowers: 51.0 cm.

Plant spread: Average: 37.5 cm.

Normal pot size: Hanging basket (8×8 cm square).

Growth rate: Moderate.

Number of leaves per plant: Average: 20.

FOLIAGE

*Average length.*—Approximately 19.8 cm.

*Average width.*—Approximately 2.7 cm.

*Shape of blade.*—Ligulate, carinate, slightly twisted lengthways.

*Aspect.*—Very slightly curved.

*Apex.*—Unequal emarginated to unequal praemorse.

*Base.*—Sheathing. Sheath length: Average 2.0 cm. Sheath width: Average 1.2 cm. Sheath color: Yellow-green; near RHS 144A.

*Margin.*—Entire.

*Texture of top surface.*—Smooth, dull.

*Texture of bottom surface.*—Smooth, dull.

*Color.*—Young foliage upper side: Green; near RHS 143A. Young foliage under side: Green; near RHS 143A. Mature foliage upper side: Green to yellow-green; a color between RHS 143A and 146A. Mature foliage under side: Yellow-green; near RHS 146B.

*Venation.*—Type: Parallel. Venation coloration: Green; near RHS N137B.

Petiole: No petioles present, leaves sessile.

FLOWERING CHARACTERISTICS

Flower bud: No flower buds observed at the time of the description.

Peduncle:

*Length.*—Approximately 32.1 cm.

*Width.*—Approximately 0.5 cm.

*Aspect.*—Approximately 20° angle to rosette.

*Strength.*—Strong.

*Texture.*—Smooth, moderately glossy.

*Color.*—Yellow-green; near RHS 144B.

INFLORESCENCE

Flowers per stem: Average: 7.

Inflorescence arrangement: Axially placed raceme.

Inflorescence height: Approximately 21.3 cm (measured from base of lowest flower to top of upper flower).

Inflorescence width: Approximately 18.7 cm.

INDIVIDUAL FLOWERS

Flower type: Zygomorphic (orchidaceous), typical shape for the genus *Vanda*.

*Shape.*—Zygomorphic, consisting of three sepals and three petals, one of which is transformed into a labellum (lip).

*Length (height).*—Approximately 11.0 cm.

*Width.*—Approximately 10.1 cm.

*Depth.*—Approximately 4.6 cm.

*Fragrance.*—No fragrance.

*Persistent.*—No.

*Quantity of petals.*—3 (2 "traditional" petals and a labellum (lip), described separately).

Petals:

*Arrangement.*—One lateral petal on each side.

*Length.*—Approximately 5.3 cm.

*Width.*—Approximately 4.4 cm.

*Shape.*—Broad ovate.

*Apex.*—Obtuse.

*Base.*—Cuneate.

*Margin.*—Entire, wavy.

*Texture.*—Upper forward surface: Smooth, dull, velvety.

*Texture.*—Lower back surface: Smooth, dull, velvety.

*Color.*—When opening, forward surface: Violet-blue to white; 91D and N155A, both colors present. When opening, back surface: Violet-blue to white; 91D and N155A, both colors present. Fully Opened, forward surface: Violet-blue to white; near 91C and 91D and N155A, all colors present. Fully Opened, back surface: Violet-blue to white; near 91C and 91D and N155A, all colors present. Fading, forward surface: Not fading. Fading, back surface: Not fading.

*Color venation fully opened, forward surface.*—Violet to violet-blue; near N88A and 93B, both colors present.

*Color venation fully opened, back surface*.—Violet-blue; near 93B.

Labellum/lip:

*Shape*.—Three-lobed, lateral lobes involute, central lobe bi-lobed, with revolute margins.

*Length*.—Approximately 2.2 cm.

*Width*.—Approximately 1.2 cm.

*Texture*.—Smooth, dull, with 3 callosities.

*Tip*.—Bi-lobed.

*Base*.—Cuneate.

*Color*.—When opening, forward surface: lateral lobes violet; near 86C and 86D (at margins), small central blotch yellow; near 13A; central lobe violet-blue; near N92C, tip greyed-purple; near N186A, callosities violet-blue; near 90D. When opening, back surface: lateral lobes violet; near N87D, central lobe darker; N88A tip greyed-purple; near N186B. Fully Opened, forward surface: lateral lobes violet; near 86C (at margins), small central blotch yellow; near 13A; central lobe violet-blue; near N92C, tip greyed-purple; near N186A, callosities violet-blue; near 90D. Fully Opened, back surface: lateral lobes violet; near N87D, central lobe darker; near N88A, tip greyed-purple; near N186B. Fading, forward surface: Not fading. Fading, back surface: Not fading.

*Color venation fully opened, forward surface*.—No venation visible on labellum.

*Color venation fully opened, back surface*.—No venation visible on labellum.

*Margin*.—Entire.

Spurs:

*Quantity*.—Average: 1.

*Length*.—Approximately 0.6 cm.

*Width*.—Approximately 0.2 cm.

*Height*.—Approximately 0.45 cm.

*Shape*.—Short triangular, in line with central lobe of labellum.

*Apex*.—Obtuse.

*Base*.—Broad cuneate.

*Margin*.—Entire.

*Texture*.—Smooth, slightly glossy.

*Color*.—Violet to greyed-purple; in between near RHS-CC 85D and N187D.

Sepals:

*Quantity*.—Average: 3; One dorsal sepal (pointing upright) and two lateral sepals.

*Length*.—Dorsal sepal approximately 5.0 cm. Lateral sepals approximately 6.1 cm.

*Width*.—Dorsal sepal approximately 5.2 cm. Lateral sepals approximately 5.6 cm.

*Shape*.—Broad ovate.

*Apex*.—Obtuse.

*Base*.—Cuneate.

*Margin*.—Entire, wavy.

*Texture*.—Smooth, dull.

*Color*.—White, near N155A, strongly veined violet to violet-blue; near N88A and 93B, both colors present.

Pedicels:

*Length*.—Approximately 5.3 cm.

*Diameter*.—Approximately 0.5 cm.

*Angle*.—Approximately 65° angle to peduncle.

*Strength*.—Very strong.

*Texture*.—Smooth, axially angled with 5 "ribs", axially twisted (due to resupination), Glossy.

*Color*.—Violet; near 85A, upper portion darker; near N87A.

REPRODUCTIVE ORGANS

Stamens, style and stigma fused into column?: Yes.

Column length: Approximately 0.6 cm.

Column diameter: Approximately 0.5 cm.

Column color: White; near NN155C.

Ovary:

*Position*.—Inferior.

*Diameter*.—Approximately 0.5 cm.

*Color*.—Violet; near 85A.

Pollinia color: Near Yellow 15A.

Drought tolerance and cold tolerance: Very strong, minimum temp is 6 degrees Celsius.

OTHER CHARACTERISTICS

Disease resistance: Good resistance to the normal diseases found in *Vanda*.

Drought tolerance and cold tolerance: Drought tolerance is typical for species. Superior cold tolerance, to approximately 6 degrees Celsius.

Fruit/seed production: No fruits/seeds detected to date.

What is claimed is:

1. A new and distinct cultivar of *Vanda* plant named 'SPCDW1110' as herein illustrated and described.

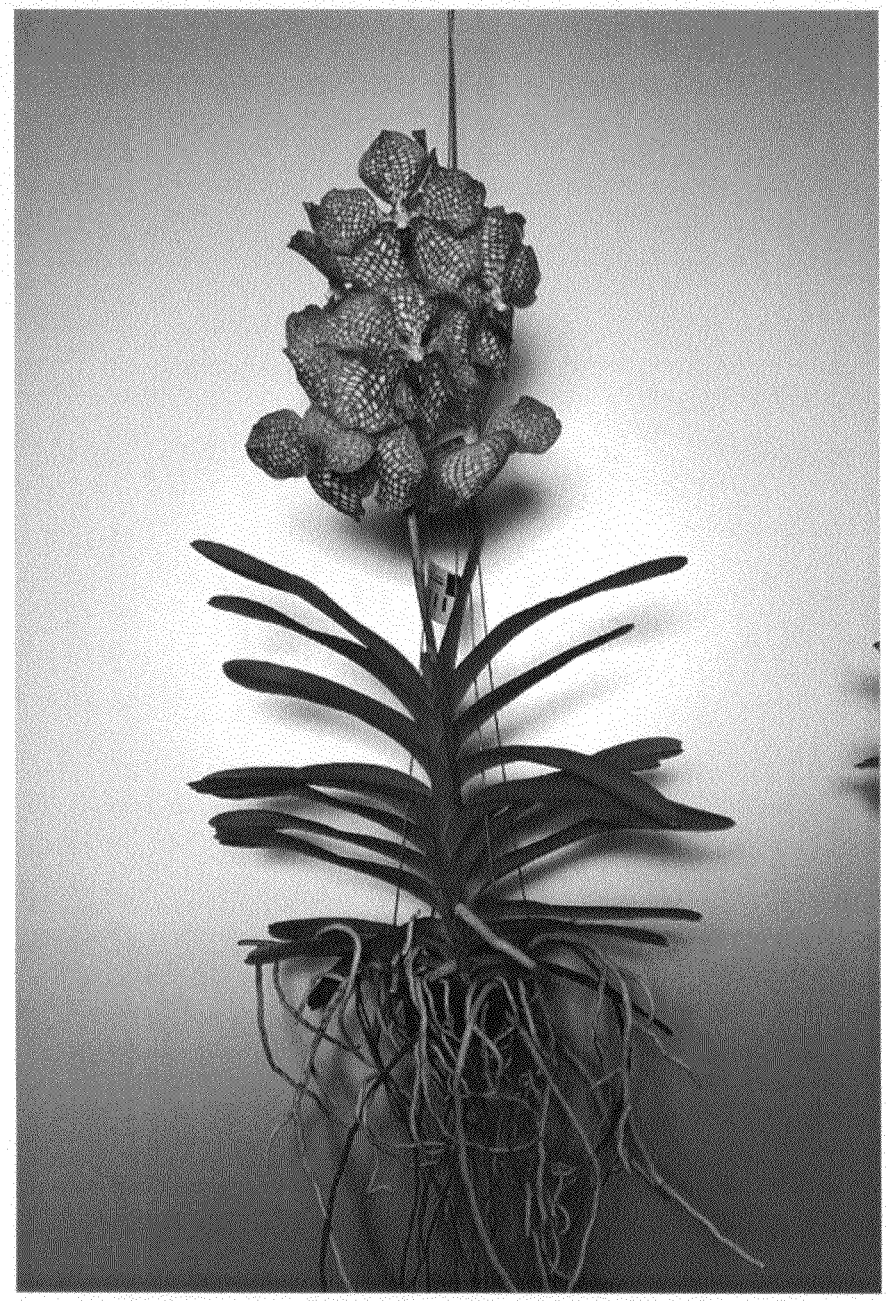

* * * * *